United States Patent [19]

Jäger et al.

[11] Patent Number: 4,514,409

[45] Date of Patent: Apr. 30, 1985

[54] COMBATING FUNGI WITH NOVEL 5-ARYLOXY-5-AZOLYL-3,3-DIMETHYL-PENT-1-EN-4-ONES AND -OLS

[75] Inventors: Gerhard Jäger, Leverkusen; Manfred Jautelat; Karl H. Büchel, both of Burscheid; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 398,028

[22] Filed: Jul. 14, 1982

[30] Foreign Application Priority Data

Aug. 1, 1981 [DE] Fed. Rep. of Germany ....... 3130435

[51] Int. Cl.³ .................... A01N 43/50; A01N 43/64; C07D 233/60; C07D 249/08
[52] U.S. Cl. .................... 514/383; 260/465 F; 548/101; 548/262; 548/341; 568/308; 568/325; 568/418; 568/649; 570/189; 570/230; 514/399
[58] Field of Search .................... 548/101, 262, 341; 424/245, 232, 269, 273 R

[56] References Cited

U.S. PATENT DOCUMENTS

| | | | |
|---|---|---|---|
| 3,812,142 | 5/1974 | Meiser et al. | 548/341 |
| 3,940,414 | 2/1976 | Kramer et al. | 548/341 |
| 3,952,002 | 4/1976 | Kramer et al. | |
| 4,147,791 | 4/1979 | Meiser et al. | 548/262 |

FOREIGN PATENT DOCUMENTS

| | | |
|---|---|---|
| 0042980 | 1/1982 | European Pat. Off. . |
| 0052424 | 5/1982 | European Pat. Off. . |
| 2918801 | 11/1980 | Fed. Rep. of Germany ...... 548/262 |

*Primary Examiner*—Alton D. Rollins
*Attorney, Agent, or Firm*—Sprung, Horn, kramer & Woods

[57] ABSTRACT

5-Aryloxy-5-azolyl-3,3-dimethylpent-1-en-4-ones and -ols of the formula

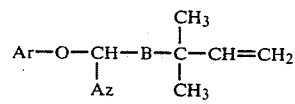

in which Ar is an optionally substituted aryl group,
Az is a 1,2,4-triazol-1-yl, 1,2,4-triazol-4-yl or imidazol-1-yl group, and
B is a keto group of a CH(OH) grouping, or addition products thereof with physiologically acceptable acids or metal salts are suitable for use as plant protection agents, and can be employed with particularly good success for combating those fungi which cause powdery mildew diseases, thus for combating Erysiphe species, Sphaerotheca species and Podosphaera species, and for combating diseases of rice.

10 Claims, No Drawings

COMBATING FUNGI WITH NOVEL 5-ARYLOXY-5-AZOLYL-3,3-DIMETHYLPENT-1-EN-4-ONES AND -OLS

The present invention relates to certain new 5-aryloxy-5-azolyl-3,3-dimethylpent-1-en-4-ones and -ols, to a process for their production, and to their use as fungicides.

It has aleady been disclosed that 4-chloro(bromo)-3,3-dimethyl-1-imidazolyl(1,2,4-triazolyl)-1-phenoxybutan-2-ones and -ols which are substituted in the phenyl part in general exhibit good fungicidal properties (see U.S. Pat. No. 4,255,434 and DE-OS (German Published Specification) No. 2,632,602). However, the action is not always completely satisfactory in some fields of use, in particular when low amounts and concentrations are used.

The present invention now provides, as new compounds, the 5-aryloxy-5-azolyl-3,3-dimethylpent-1-en-4-ones and -ols of the general formula $$Ar-O-CH-B-\underset{\underset{CH_3}{|}}{\overset{\overset{CH_3}{|}}{C}}-CH=CH_3 \quad (I)$$
$$\phantom{Ar-O-CH}\underset{Az}{|}$$

in which
Ar represents an optionally substituted aryl group,
Az represents a 1,2,4-triazol-1-yl, 1,2,4-triazol-4-yl or imidazol-1-yl group, and
B represents a keto group or a CH(OH) grouping,
and their physiologically acceptable acid addition salts or metal salt complexes thereof.

Those compounds of the formula (I) in which B represents the CH(OH) group possess two asymmetric carbon atoms; they can therefore be present as the two geometrical isomers (erythro and threo form), which can occur in different proportions. In both cases, they are present as optical isomers. All isomers are claimed according to the invention.

According to the present invention we provide a process for the production of a compound of the present invention characterized in that a halogenoether-ketone of the general formula $$Ar-O-\underset{\underset{Hal}{|}}{CH}-CO-\underset{\underset{CH_3}{|}}{\overset{\overset{CH_3}{|}}{C}}-CH=CH_3 \quad (II)$$

in which
Ar has the meaning given above and
Hal represents a chlorine or bromine atom,
is reached with 1,2,4-triazole or imidazole in the presence of an acid-binding agent and, if appropriate, in the presence of a diluent, and the resulting keto derivative of the formula (I) is reduced if a compound of formula (I) in which B represents a CH(OH) grouping is required; and, if desired, an acid or a metal salt is subsequently added onto the compound of formula (I).

The novel compounds of the present invention exhibit powerful fungicidal properties. In this respect, the compounds according to the present invention surprisingly exhibit a better fungicidal activity than the 4-chloro (bromo)-3,3-dimethyl-1-imidazolyl(1,2,4-triazolyl)-1-phenoxybutan-2-ones and -ols substituted in the phenyl part, which are known from the state of the art and are similar compounds chemically and with respect to their action. The compounds according to the present invention thus represent an enrichment of the art.

Preferred compounds according to the present invention are those, in which
Ar represents a phenyl group which is optionally monosubstituted or polysubstituted by identical or different substituents (preferably selected from halogen, alkyl having 1 to 4 carbon atoms, halogenoalkyl having 1 or 2 carbon atoms and 1 to 5 identical or different halogen atoms-such as fluorine atoms and chlorine atoms, alkoxycarbonyl having 1 to 4 carbon atoms in the alkyl part, nitro, cyano or phenyl which is optionally substituted by halogen and/or alkyl having 1 or 2 carbon atoms); and
Az and B have the abovementioned meanings.

Particularly preferred compounds according to the present invention are those, in which
Ar represents a phenyl group which is optionally monosubstituted to trisubstituted by identical or different substituents selected from fluorine, chlorine, bromine, methyl, ethyl, trifluoromethyl, methoxycarbonyl, ethoxycarbonyl, nitro, cyano, phenyl and chlorophenyl, and
Az and B have the abovementioned meanings.

In addition to the compounds mentioned in the preparative Examples, the following compounds of the general formula (I) may be mentioned in particular:

TABLE 1

$$Ar-O-CH-B-\underset{\underset{CH_3}{|}}{\overset{\overset{CH_3}{|}}{C}}-CH=CH_2 \quad (I)$$
$$\phantom{Ar-O-CH}\underset{Az}{|}$$

| Ar | Az | B |
|---|---|---|
|  Br—⟨phenyl⟩— | 1,2,4-Triazol-1-yl | CO and CH(OH) |
| 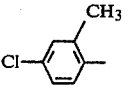 Cl—⟨phenyl(CH₃)⟩— | 1,2,4-Triazol-1-yl | CO and CH(OH) |
|  ⟨phenyl-Cl⟩ | 1,2,4-Triazol-1-yl | CO and CH(OH) |
| 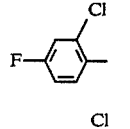 F—⟨phenyl-Cl⟩— | 1,2,4-Triazol-1-yl | CO and CH(OH) |
| 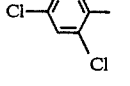 Cl—⟨phenyl(Cl,Cl)⟩— | 1,2,4-Triazol-1-yl | CO and CH(OH) |
| 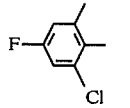 F—⟨phenyl(Cl,Cl)⟩— | 1,2,4-Triazol-1-yl | CO and CH(OH) |
| 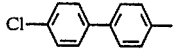 Cl—⟨phenyl⟩—⟨phenyl⟩— | 1,2,4-Triazol-1-yl | CO and CH(OH) |

TABLE 1-continued $$Ar-O-CH-B-\underset{\underset{CH_3}{|}}{\overset{\overset{CH_3}{|}}{C}}-CH=CH_2 \quad (I)$$
$$\phantom{Ar-O-CH-B-}|$$
$$\phantom{Ar-O-CH-B}Az$$

| Ar | Az | B |
|---|---|---|
| Br–⌬– | Imidazol-1-yl | CO and CH(OH) |
| Cl–⌬(CH₃)– | Imidazol-1-yl | CO and CH(OH) |
| ⌬(Cl)– (ortho) | Imidazol-1-yl | CO and CH(OH) |
| F–⌬(Cl)– | Imidazol-1-yl | CO and CH(OH) |
| Cl–⌬(Cl)(Cl)– | Imidazol-1-yl | CO and CH(OH) |
| F–⌬(Cl)(Cl)– | Imidazol-1-yl | CO and CH(OH) |
| Cl–⌬–⌬– | Imidazol-1-yl | CO and CH(OH) |

If, for example, 5-bromo-5-(4-chlorophenoxy)-3,3-dimethylpent-1-en-4-one and imidazole are used as starting materials, the course of the reaction according to the present invention is illustrated by the following equation:

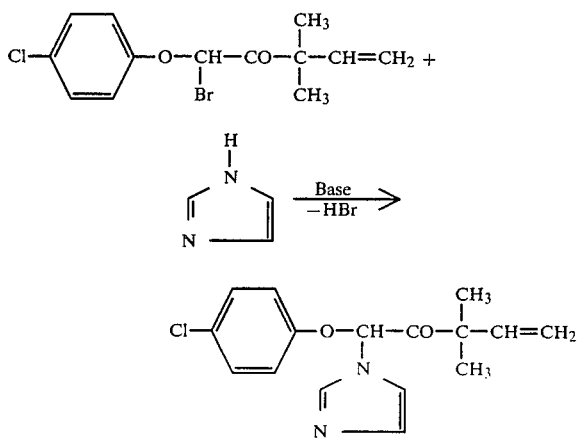

If, for example, 5-(4-chlorophenoxy)-3,3-dimethyl-5-(imidazol-1-yl)-pent-1-en-4-one and sodium borohydride are used as starting materials, the course of the reduction step of the reaction according to the present invention is illustrated by the following equation:

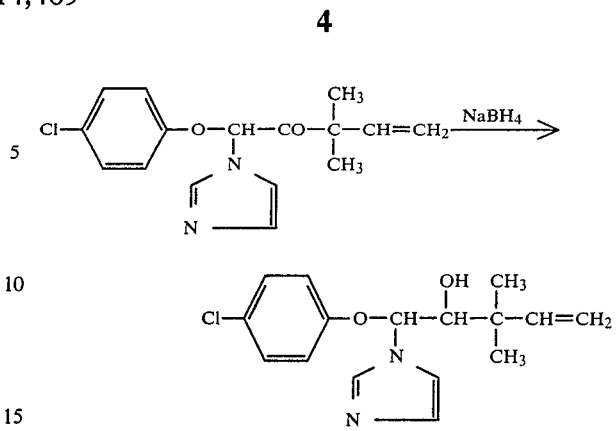

Preferred halogenoether-ketones of formula (II) to be used as starting materials in carrying out the process according to the invention are those in which Ar represents those radicals which have already been mentioned in connection with the description of the preferred and particularly preferred compounds according to the present invention.

The halogenoether-ketones of the formula (II) are novel; however, they can be prepared by known processes, by replacing in a customary manner, for example in an ether-ketone of the general formula

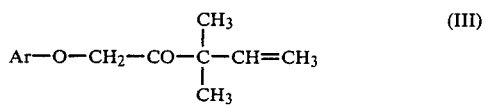

in which

Ar has the meaning given above,
one of the two active hydrogen atoms by a chlorine or bromine atom. The resulting halogenoether-ketones of the formula (II) can be directly further reacted, without isolation (see also the preparative examples).

The ether-ketones of the formula (III), likewise, are novel; however, some of them form the subject of United States Patent Application Ser. No. 335,942, filed Dec. 30, 1981, now U.S. Pat. No. 4,399,309.

According to the one-pot process given in the above copending application, an ether-ketone of the formula (III) can be obtained when an aryloxy-diene derivative of the general formula

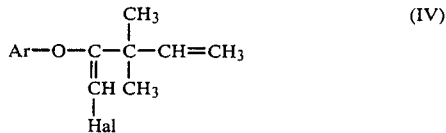

in which

Ar and Hal have the meanings given above,
is subjected to acid hydrolysis in the temperature range between +20° and 150° C., and, after the addition of a basic compound (such as potassium carbonate), the reaction is subsequently brought to completion in the temperature range mentioned, under slightly alkaline reaction conditions.

The aryloxy-diene derivatives of the formula (IV) can be obtained in a simple manner from olefins, by hydrogen halide addition, subsequent addition to a vinylidene halide in the presence of acid catalysts (for example aluminum chloride) and reaction of the resulting adduct with alkali metal phenolates (as described in U.S. application Ser. No. 281,614, filed July 9, 1981, now abandoned, and U.S. Ser. No. 329,959, filed Dec. 11, 1981, now U.S. Pat. No. 4,460,793.

The ether-ketone of the formula (III) can also be obtained by reacting an appropriate phenol with 5-chloro-(bromo)-3,3-dimethylpent-1-en-4-one of the formula

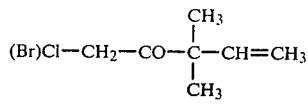 (V)

in the presence of a strong base (such as potassium carbonate) and in the presence of an inert organic solvent (such as acetone) at a temperature between 20° and 100° C.

The 5-chloro(bromo)-3,3-dimethylpent-1-ene-4-one of the formula (V) is novel; however, it is the subject of previous United States patent application Ser. No. 329,959, filed Dec. 11, 1981, now U.S. Pat. No. 4,460,793 and is obtained by reacting 1,1-dichloro-3,3-dimethyl-1,4-pentadiene, for example, with an alkali metal phenolate and then subjecting the resulting reaction product to acid hydrolysis (see also the preparative Examples herein).

Inert organic solvents are suitable diluents for the reaction according to the invention. These preferably include ketones (such as diethyl ketone and preferably acetone and methyl ethyl ketone); nitriles (such as propionitrile or preferably, acetonitrile); alcohols (such as ethanol or isopropanol); ethers (such as tetrahydrofuran or dioxane); benzene, toluene, formamides (such as, preferably, dimethylformamide); and halogenated hydrocarbons.

The reaction according to the invention is carried out in the presence of an acid-binding agent. Any of the inorganic or organic acid-binding agents which can be customarily employed can be added, such as alkali metal carbonates (for example sodium carbonate, potassium carbonate and sodium bicarbonate) or $C_1$ to $C_6$ tertiary alkylamines, cycloalkylamines or aralkylamines (for example triethylamine, N,N-dimethylcyclohexylamine, dicyclohexylamine, N,N-dimethylbenzylamine, and furthermore pyridine and diazabicyclooctane). An appropriate excess of triazole or imidazole is preferably used.

The reaction temperatures can be varied within a relatively wide range. In general, the reaction is carried out at a temperature between 20° and 150° C., preferably between 60° and 120° C. When a solvent is present, the reaction is advantageously carried out at the boiling point of the particular solvent.

In carrying out the process according to the invention, 2 mols of triazole or imidazole and 1 to 2 mols of the acid-binding agent are preferably employed per mol of the compounds of the formula (II). Generally, to isolate the compounds of the formula (I), the solvent is distilled off, the residue is taken up with an organic solvent and the solution is washed with water. The organic phase can be dried over sodium sulphate and freed in vacuo from solvent. The residue can be purified by distillation or recrystallization or salt formation and recrystallization.

The reduction according to the invention is effected in a customary manner, for example by reaction with complex hydrides, if appropriate in the presence of a diluent, or by reaction with aluminum isopropylate in the presence of a diluent.

If a complex hydride is used, a polar organic solvent is a suitable diluent for the reaction according to the invention. These solvents include, as preferences, alcohols (such as methanol, ethanol, butanol or isopropanol) and ethers (such as diethyl ether or tetrahydrofuran). The reaction is carried out in general at a temperature between 0° and 30° C., preferably between 0° and 20° C. In this reaction, about 1 mol of a complex hydride (such as sodium borohydride or lithium alanate) is employed per mol of the ketone of the formula (I). To isolate the reduced compounds of the formula (I), the residue is taken up in dilute hydrochloric acid, and the solution is then rendered alkaline and extracted with an organic solvent. Further working-up is effected in a customary manner.

If aluminum isopropylate is used, an alcohol (such as isopropanol) or an inert hydrocarbon (such as benzene) is a preferred diluent for the reaction according to the invention. The reaction temperatures can again be varied in a relatively wide range; in general, the reaction is carried out at a temperature between 20° and 120° C., preferably between 50° and 100° C. To carry out the reaction, about 0.3 to 2 mols of aluminum isopropylate are employed per mol of the ketone of the formula (I). To isolate the reduced compounds of the formula (I), the excess solvent is removed in vacuo and the resulting aluminum compounds are decomposed with dilute sulphuric acid or sodium hydroxide solution. Further working-up is effected in a customary manner.

Any of the physiologically tolerated acids can be used for the preparation of acid addition salts of the compounds of the formula (I). These acids include, as preferences, hydrogen halide acids (such as hydrobromic acid and, preferably, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid (for example hydrochloric acid) and they can be isolated in a known manner, for example by filtration, and if appropriate purified by washing with an inert organic solvent or by recrystallization.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are derived from physiological acids. These include, as preferences, hydrogen halide acids (such as hydrochloric acid and hydrobromic acid), phosphoric acid, nitric acid and sulphuric acid.

The metal salt complexes of the compounds of the formula (I) can be obtained in a simple manner by customary processes, thus, for example, by dissolving the metal salt in alcohol (for example ethanol) and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, for example against the powdery mildew of barely causative organism (Erysiphe graminis), and Sphaerotheca species, for example, against the powdery mildew of cucumber causative organism (Sphaerotheca fuliginea), as well as Podosphaera species, for example against the powdery mildew of apple causative organism (Podosphaera leucotricha); and also for combating diseases of rice, such as Pyricularia oryzae. The substances according to the invention possess, in addition, a broad in vitro fungicidal action.

When used in appropriate amounts, the substances according to the invention also exhibit herbicidal or plant growth-regulating activity.

The active compounds can be converted to the customary formulations such as solutions, emulsions, suspensions, powders, foams, pastes, granules, aerosols, natural and synthetic materials impregnated with active compound, very fine capsules in polymeric substances and in coating compositions for seed, and in formulations used with burning equipment, such as fumigating cartridges, fumigating cans and, fumigating coils as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules or organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.0001%.

In the treatment of seed, generally amounts of active compound of 0.001 to 50 g per kilogram of seed, preferably 0.01 to 10 g, are required.

For the treatment of soil, generally active compound concentrations of 0.00001 to 0.1% by weight, preferably 0.0001 to 0.02%, are required at the place of action.

The present invention also provides fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

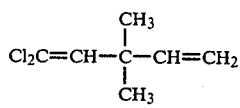
(a)

201.5 g (1 mol) of 3,3-dimethyl-1,1,5-trichloropent-1-ene were slowly added dropwise to 1,000 ml of quinoline at from 225° to 230° C., and distillate was taken off simultaneously via the top of the column. The temperature was increased until the quinoline boiled, and a total of 126 g of distillate were isolated and again fractionated. 121 g (73% of theory) of 1,1-dichloro-3,3-dimethyl-1,4-pentadiene of boiling point 49° to 53° C./20 mm Hg were obtained.

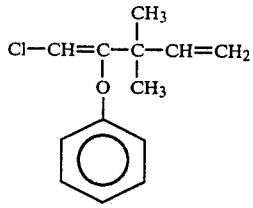
(b)

116 g (1 mol) of sodium phenolate and 82.5 g (0.5 mole) of 1,1-dichloro-3,3-dimethyl-1,4-pentadiene in 500 ml of dimethylformamide were heated under reflux for 8 hours. The solution was diluted with methylene chloride and extracted by shaking with dilute sodium hydroxide solution. After the methylene chloride phase had been dried over sodium sulphate, the solvent was stripped off in vacuo. The residual crude product was distilled in vacuo. 93.6 g (84% of theory) of 1-chloro-3,3-dimethyl-2-phenoxy-1,4-pentadiene of boiling point 80° to 90° C./0.5 mm Hg were obtained.

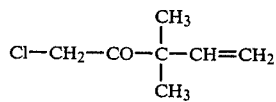
(c)

57 g (0.256 mol) of 1-chloro-3,3-dimethyl-2-phenoxy-1,4-pentadiene in a mixture of 250 ml of formic acid and 50 ml of concentrated hydrochloric acid were heated to 40° C. in the course of 1 hour. The mixture was then diluted with 400 ml of methylene chloride and ice, and was extracted three times by shaking with 2N sodium hydroxide solution. After the methylene chloride phase had been dried over sodium sulphate, the solvent was removed. 36 g of product (96% of theory) remained and were distilled. 32.2 g (86% of theory) of 5-chloro-3,3-dimethylpent-1-en-4-one of boiling point 81° to 84° C./24 mm Hg were obtained.

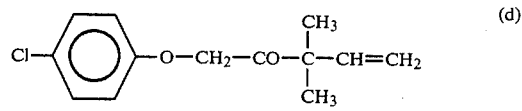
(d)

92.9 g (0.723 mol) of 4-chlorophenol were heated to the boil with 99.7 g (0.723 mol) of finely powdered potassium carbonate in 500 ml of acetone. 106 g (0.723 mol) of 5-chloro-3,3-dimethylpent-1-en-4-one were added dropwise to the mixture in the course of 30 minutes, while stirring vigorously. After the mixture had been heated under reflux for four hours, it was cooled to 20° C. and filtered off from the inorganic salts, and the filtrate was concentrated. After the liquid residue had been distilled, 136.3 g (79% of theory) of 5-(4-chlorophenoxy)-3,3-dimethylpent-1-en-4-one of boiling point 111° to 113° C./0.07 mm Hg were obtained.

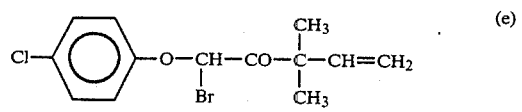
(e)

12.5 g (0.07 mol) of N-bromosuccinimide were added to a solution of 16.7 g (0.07 mol) of 5-(4-chlorophenoxy)-3,3-dimethylpent-1-en-4-one and a pinch of azoisobutyronitrile in 200 ml of tetrachloromethane. The mixture was then heated at the boil for 8 hours, under UV irradiation. The mixture was then cooled to 5° C. and filtered off from the precipitated succinimide. The filtrate was concentrated in vacuo. 23 g of crude 5-bromo-5-(4-chlorophenoxy)-3,3-dimethylpent-1-en-4-one were obtained as an oil, which was directly reacted further.

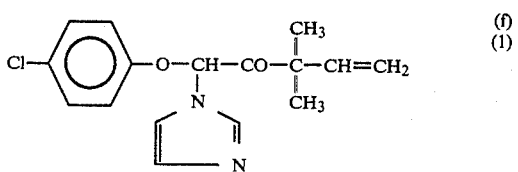
(f)
(1)

23 g of crude 5-bromo-5-(4-chlorophenoxy)-3,3-dimethylpent-1-en-4-one, dissolved in 30 ml of acetonitrile, were added dropwise to a solution of 28.6 g (0.42 mol) of imidazole in 250 ml of acetonitrile, in the course of 5 minutes. The mixture was then heated to the boil for a further 3 hours and the solution was concentrated under reduced pressure. The oily residue was taken up in 200 ml of ethyl acetate and the mixture was washed with three times 50 ml of water. After the organic phase had been dried over anhydrous sodium sulphate, it was concentrated by evaporation, the residue was taken up in 200 ml of acetone and a filtered solution of 20.2 g (0.07 mol) of naphthalene-1,5-disulphonic acid in 100 ml of acetone was added. The precipitated salt was filtered off under suction, 100 ml of water and 100 ml of dichloromethane were added to it, and the mixture was then rendered alkaline with 10% strength sodium carbonate solution. The organic phase was separated off and concentrated. The oily residue crystallized on trituration with ether/petroleum ether. 7.4 g (34.7% of theory) of 5-(4-chlorophenoxy)-3,3-dimethyl-5-(imidazol-1-yl)- pent-1-en-4-one of melting point 72° to 74° C. were obtained.

EXAMPLE 2

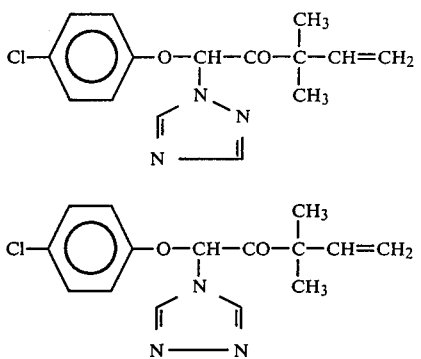

89 g (0.28 mol) of 5-bromo-5-(4-chlorophenoxy)-3,3-dimethylpent-1-en-4-one, dissolved in 120 ml of acetonitrile, were added dropwise, in the course of 30 minutes, to a solution of 115.9 g (1.68 mols) of 1,2,4-triazole in 1,000 ml of acetonitrile at 50° C. After the solution had been heated at the boil for three hours, the solvent was distilled off and the residue was taken up in 300 ml of ethyl acetate. The solution was washed three times with 50 ml of water, and the organic phase, after having been dried over anhydrous sodium sulphate, was concentrated by evaporation under reduced pressure. The residual oil was dissolved in 400 ml of acetone, and a solution of 80.6 g of naphthalene-1,5-disulphonic acid in 400 ml of acetone was added. The salt which had crystallized out was filtered off under suction and washed with acetone, 250 ml each of water and dichloromethane were stirred with the salt, and the mixture was then rendered alkaline with a 10% strength sodium carbonate solution. The oil which remained after the organic phase had been evaporated off was dissolved in a small amount of ether, and petroleum ether was then slowly added to the solution. The product which crystallized out in the process was filtered off and washed with a small amount of ether/petroleum ether. 17.1 g (20% of theory) of 5-(4-chlorophenoxy)-3,3-dimethyl-5-(1,2,4-triazol-4-yl)-pent-1-en-4-one (Compound 3) of melting point 124° to 126° C. were obtained.

The filtrate was concentrated and the oily residue was taken up in chloroform/ethyl acetate (1:2). After the solution had been filtered over a silica gel column, 17.5 g (20.4% of theory) of 5-(4-chlorophenoxy)-3,3-dimethyl-5-(1,2,4-triazol-1-yl)-pent-1-en-4-one (Compound 2) of refractive index $n_D^{20} = 1.5419$ were obtained.

EXAMPLE 3

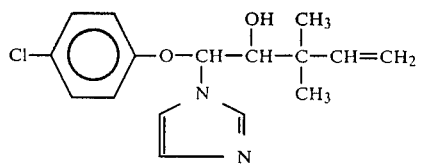

3.8 g (0.1 mol) of sodium boranate were introduced in portions into a solution of 15.3 g (0.05 mol) of 5-(4-chlorophenoxy)-3,3-dimethyl-5-(imidazol-1-yl)-pent-1-en-4-one (obtained as described in Example 1) in 150 ml of methanol, the mixture being cooled externally. After 6 hours, the reaction mixture was adjusted to pH 6 with dilute acetic acid, and was concentrated by evaporation under reduced pressure. The residue was taken up in ethyl acetate, and the solution was washed once with dilute sodium bicarbonate solution and three times with water, dried over sodium sulphate and thereafter concentrated in vacuo. The oily residue was dissolved in a small amount of ether and petroleum ether was added to the solution. The resulting precipitate was separated off, washed with a small amount of petroleum ether and dried. 12.2 g (79.7% of theory) of 5-(4-chlorophenoxy)-3,3-dimethyl-5-(imidazol-1-yl)-pent-1-en-4-ol of melting point 88° to 90° C. were obtained.

The compounds of Table 2 below, of the general formula

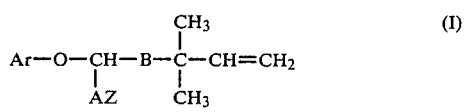

were obtained in a corresponding manner:

TABLE 2

| Compound No. | Ar | Az | B | Physical constants |
|---|---|---|---|---|
| 5 | ⌬—⌬— | —N⟨imidazole⟩ | CO | resin |
| 6 | 2,4-Cl₂—C₆H₃— | —N⟨imidazole⟩ | CO | resin |
| 7 | F—C₆H₄— | —N⟨imidazole⟩ | CO | $n_D^{20} = 1.5301$ |
| 8 | F—C₆H₄— | —N⟨imidazole⟩ | CO | m.p.: 242° C. (decomposition) (× ½ NDS)* |
| 9 | 2,4-Cl₂—C₆H₃— | —N⟨1,2,4-triazole⟩ | CO | oil |
| 10 | ⌬—⌬— | —N⟨1,2,4-triazole⟩ | CO | m.p.: 152–53° C. |
| 11 | F—C₆H₄— | —N⟨1,2,4-triazole⟩ | CO | m.p.: 91–94° C. |

TABLE 2-continued

| Compound No. | Ar | Az | B | Physical constants |
|---|---|---|---|---|
| 12 | biphenyl- | -N(=N imidazole) | CH(OH) | m.p.: 132° C. |
| 13 | 3,4-dichlorophenyl- | -N(=N imidazole) | CH(OH) | oil |
| 14 | 4-fluorophenyl- | -N(=N imidazole) | CH(OH) | oil |
| 15 | 4-chlorophenyl- | -N(N= 1,2,4-triazole) | CH(OH) | resin |
| 16 | 4-chlorophenyl- | -N(N= 1,2,4-triazole) | CH(OH) | m.p.: 167–69° C. (× ½ NDS)* |
| 17 | 4-chlorophenyl- | -N(=N 1,2,4-triazole) | CH(OH) | m.p.: 200–01° C. (form A)** |
| 18 | 4-chlorophenyl- | -N(=N 1,2,4-triazole) | CH(OH) | m.p.: 170–90° C. |

*NDS = naphthalene-1,5-disulphonic acid
**form A = one of the two possible geometrical isomers The fungicidal activity of the compounds of this invention is illustrated by the following biotest examples.

In these examples, the compounds according to the present invention are each identified by the number (given in brackets) from Examples 1 to 3 and Table 2.

The known comparison compounds are identified as follows:

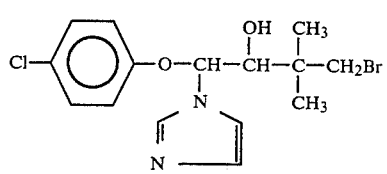

(A)

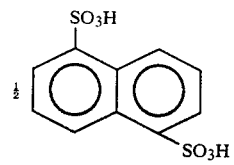

(B)

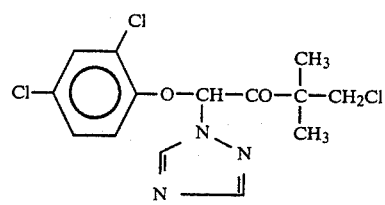

(C)

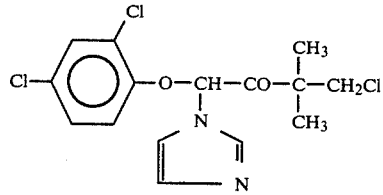

(D)

EXAMPLE 4

Podosphaera test (apple) /protective

Solvent: 4.7 parts by weight of acetone.
Emulsifier: 0.3 part by weight of alkylaryl polyglycol ether.

To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated by dusting with conidia of the powdery mildew of apple causative organism (*Podosphaera leucotricha*).

The plants were then placed in a greenhouse at 23° C. and a relative atmospheric humidity of about 70%.

Evaluation was carried out 9 days after the inoculation.

In this test, a clearly superior activity compared with the prior art is shown, for example, by the compounds (1), (2), (4), (6), (15), (5) and (9).

EXAMPLE 5

Sphaerotheca test (cucumber) /protective

Solvent: 4.7 parts by weight of acetone.
Emulsifier: 0.3 part by weight of alkylaryl polyglycol ether.

To produce a suitable preparation of active compound, 1 part by weight of active compound was mixed with the stated amounts of solvent and emulsifier, and the concentrate was diluted with water to the desired concentration.

To test for protective activity, young plants were sprayed with teh preparation of active compound until dripping wet. After the spray coating had dried on, the plants were dusted with conidia of the fungus Sphaerotheca fuliginea.

The plants were then placed in a greenhouse at 23° to 24° C. and at a relative atmospheric humidity of about 75%.

Evaluation was carried out 10 days after the inoculation.

In this test, a clearly superior activity compared with the prior art was shown, for example, by the compounds (2), (15), (6), (5) and (9).

EXAMPLE 6

Erysiphe test (barley) /protective

Solvent: 100 parts by weight of dimethylformamide.
Emulsifier: 0.25 part by weight of alkylaryl polyglycol ether.

To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f.sp.hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (2), (15), (9), (1), (4), (5) and (6).

EXAMPLE 7

Erysiphe test (barley) /seed treatment

The active compounds were used as dry dressings. These were prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of Erysiphe graminis f. sp. hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art was shown, for example, by the compounds (2), (15), (9) and (4).

It will be understood that the specification and examples are illustrative but not limitative of the present invention and that other embodiments within the spirit and scope of the invention will suggest themselves to those skilled in the art.

We claim:

1. A 5-aryloxy-5-azolyl-3,3-dimethylpent-1-en-4-one or -ol of the formula

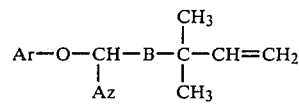

in which
Ar is a phenyl group or a phenyl group substituted by at least one substituent selected from the group consisting of halogen, alkyl having 1 to 4 carbon atoms, halogenoalkyl having 1 or 2 carbon atoms and 1 to 5 identical or different halogen atoms, alkoxycarbonyl having 1 to 4 carbon atoms in the alkyl part, nitro, cyano or phenyl which is optionally substituted by halogen and/or alkyl having 1 or 2 carbon atoms.
Az is a 1,2,4-triazol-1-yl, 1,2,4-triazol-4-yl or imidazol-1-yl group, and
B is a keto group or a CH(OH) grouping, or an addition product thereof with a physiologically acceptable acid or a metal salt.

2. A compound or addition product according to claim 1, in which
Ar is a phenyl group, or a phenyl group substituted by at least one substituent selected from the group consisting of fluorine, chlorine, bromine, methyl, ethyl, trifluoromethyl, methoxycarbonyl, ethoxycarbonyl, nitro, cyano, phenyl and chlorophenyl.

3. A compound according to claim 1, wherein such compound is 5-(4-chlorophenoxy)-3,3 -dimethyl-5-(1,2,4-triazol-1-yl)-pent-1-ene-4-one of the formula

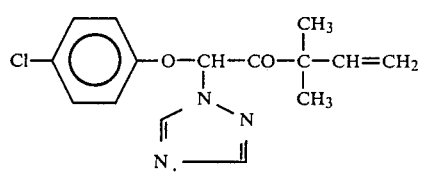

or an addition product thereof with a physiologically acceptable acid or metal salt.

4. A compound according to claim 1, wherein such compound is 5-(4-chlorophenoxy)-3,3-dimethyl-5-(imidazol-1-yl)-pent-1-en-4-ol of the formula

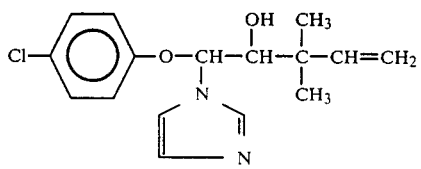

or an addition product thereof with a physiologically acceptable acid or metal salt.

5. A compound according to claim 1, wherein such compound is 5-(4-biphenylyloxy)-3,3-dimethyl-5-(imidazol-1-yl)-pent-1-en-4-one of the formula

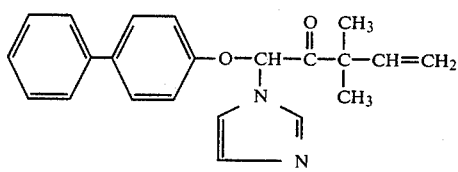

or an addition product thereof with a physiologically acceptable acid or metal salt.

6. A compound according to claim 1, wherein such compound is 5-(2,4-dichlorophenoxy)-3,3-dimethyl-5-(1,2,4-triazol-1-yl)-pent-1-en-4-one of the formula

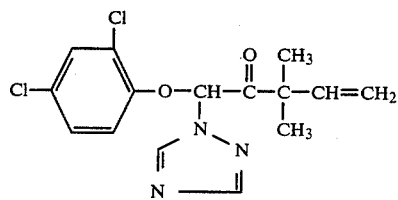

or an addition product thereof with a physiologically acceptable acid or metal salt.

7. A compound according to claim 1, wherein such compound is 5-(4-chlorophenoxy)-3,3-dimethyl-5-(1,2,4-triazol-1-yl)-pent-1-en-4-ol of the formula

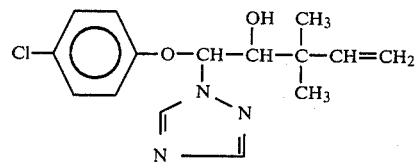

or an addition product thereof with a physiologically acceptable acid or metal salt.

8. A fungicidal composition comprising a fungicidally effective amount of a compound or addition product according to claim 1 in admixture with a diluent.

9. A method of combating fungi comprising applying to the fungi, or to a habitat thereof, a fungicidally effective amount of a compound or addition product according to claim 1.

10. The method according to claim 9, wherein such compound is
- 5-(4-chlorophenoxy)-3,3-dimethyl-5-(1,2,4-triazol-1-yl)-pent-1-en-4-one,
- 5-(4-chlorophenoxy)-3,3-dimethyl-5-(imidazol-1-yl)-pent-1-en-4-ol,
- 5-(4-biphenylyloxy)-3,3-dimethyl-5-(imidazol-1-yl)-pent-1-en-4-one,
- 5-(2,4-dichlorophenoxy)-3,3-dimethyl-5-(1,2,4-triazol-1-yl)-pent-1-en-4-one or
- 5-(4-chlorophenoxy)-3,3-dimethyl-5-(1,2,4-triazol-1-yl)-pent-1-en-4-ol, or an addition product thereof with a physiologically acceptable acid or metal salt.

* * * * *

UNITED STATES PATENT AND TRADEMARK OFFICE
CERTIFICATE OF CORRECTION

PATENT NO. : 4,514,409

DATED : April 30, 1985

INVENTOR(S) : Gerhard Jäger, et al

It is certified that error appears in the above-identified patent and that said Letters Patent is hereby corrected as shown below:

| | |
|---|---|
| Col. 1, line 10 | Correct spelling of "already" |
| Col. 1, lines 25, 48; Col. 4, lines 31, 51 and Col. 5, line 12 | End of formula delete "=$CH_3$" and substitute -- =$CH_2$-- |
| Col. 1, line 55 | Delete "reached" and substitute --reacted-- |
| Col. 7, line 22 | Delete "barely" and substitute --barley-- |
| Col. 8, line 54 | Delete "0.0001 %" and substitute --0.001 %-- |
| Col. 9, line 42 | Delete "mole" and substitute --mol-- |
| Col. 18, line 5 | Delete -- -$CH_2$ -- beginning of formula and substitute: |

Signed and Sealed this

*Twenty-ninth* Day of *October 1985*

[SEAL]

*Attest:*

*Attesting Officer*

DONALD J. QUIGG

*Commissioner of Patents and Trademarks—Designate*